United States Patent
Kawajiri et al.

(10) Patent No.: US 11,931,500 B2
(45) Date of Patent: Mar. 19, 2024

(54) PRESSURE DETECTOR

(71) Applicant: Nikkiso Company Limited, Tokyo (JP)

(72) Inventors: Hiroyuki Kawajiri, Shizuoka (JP); Shingo Okamoto, Shizuoka (JP); Ryo Kato, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 649 days.

(21) Appl. No.: 17/093,825

(22) Filed: Nov. 10, 2020

(65) Prior Publication Data

US 2021/0052797 A1    Feb. 25, 2021

Related U.S. Application Data

(63) Continuation of application No. PCT/JP2019/019396, filed on May 15, 2019.

(30) Foreign Application Priority Data

May 16, 2018   (JP) ................................. 2018-094465

(51) Int. Cl.
   *A61M 1/36*      (2006.01)
   *A61M 1/16*      (2006.01)
   (Continued)

(52) U.S. Cl.
   CPC ........ *A61M 1/3641* (2014.02); *A61M 1/1605* (2014.02); *A61M 1/36* (2013.01);
   (Continued)

(58) Field of Classification Search
   CPC .... A61M 1/1605; A61M 1/36; A61M 1/3641; A61M 2205/3331; A61M 2205/7536;
   (Continued)

(56) References Cited

U.S. PATENT DOCUMENTS 4,908,493 A   3/1990   Susemihl
5,221,271 A   6/1993   Nicholson et al.
(Continued)

FOREIGN PATENT DOCUMENTS

DE   102008034920 A1   9/2009
EP       0074733 A1   3/1983
(Continued)

OTHER PUBLICATIONS

Potentially related U.S. Appl. No. 17/128,705, filed Dec. 21, 2020 entitled "Method and Apparatus of Manufacturing Medical Device".
(Continued)

*Primary Examiner* — John Kim
(74) *Attorney, Agent, or Firm* — Young Basile Hanlon & MacFarlane, P.C.

(57) ABSTRACT

A pressure detector that includes a case connectable to a flow route for liquid, and a membrane member provided in the case and with which a liquid-phase portion to be supplied with the liquid in the flow route and a gas-phase portion to be supplied with gas are separated from each other, the membrane member being displaceable in accordance with a pressure of the liquid supplied to the liquid-phase portion, the pressure detector detecting the pressure of the liquid in the flow route by detecting a pressure in the gas-phase portion. The gas-phase portion has an opening through which the gas is allowed to be introduced or discharged in accordance with the displacement of the membrane member, and a secured portion secured for the introduction or discharge of the gas through the opening during the displacement of the membrane member toward a side of the gas-phase portion.

10 Claims, 10 Drawing Sheets

(51) Int. Cl.
*G01L 7/08* (2006.01)
*G01L 11/00* (2006.01)
*G01L 19/00* (2006.01)
*G01L 19/14* (2006.01)

(52) U.S. Cl.
CPC ............... *G01L 7/08* (2013.01); *G01L 11/00* (2013.01); *G01L 19/00* (2013.01); *G01L 19/0023* (2013.01); *G01L 19/14* (2013.01); *A61M 2205/3331* (2013.01); *A61M 2205/7536* (2013.01)

(58) Field of Classification Search
CPC ......... B01D 61/362; G01L 7/08; G01L 11/00; G01L 19/00; G01L 19/0023; G01L 19/14
See application file for complete search history.

(56) References Cited

U.S. PATENT DOCUMENTS

| | | | |
|---|---|---|---|
| 6,392,208 | B1 | 5/2002 | Arx |
| 8,092,414 | B2 | 1/2012 | Schnell et al. |
| 8,960,010 | B1 | 2/2015 | Crnkovich et al. |
| 10,775,252 | B2 | 9/2020 | Funamura et al. |
| 2003/0115965 | A1 | 6/2003 | Mittelstein et al. |
| 2007/0118153 | A1 | 5/2007 | Funamura et al. |
| 2007/0295093 | A1 | 12/2007 | Reiter et al. |
| 2009/0071258 | A1 | 3/2009 | Kouda et al. |
| 2010/0186518 | A1 | 7/2010 | Jonsson et al. |
| 2015/0306299 | A1 | 10/2015 | Stuva et al. |
| 2017/0312412 | A1 | 11/2017 | Mochizuki |
| 2017/0340798 | A1 | 11/2017 | Lindley et al. |
| 2020/0198459 | A1 | 6/2020 | Bouffier et al. |
| 2021/0106744 | A1 | 4/2021 | Okamoto et al. |

FOREIGN PATENT DOCUMENTS

| | | | |
|---|---|---|---|
| EP | 0330891 | A1 | 9/1989 |
| JP | S62-051630 | B2 | 10/1987 |
| JP | H02-001275 | A | 1/1990 |
| JP | H09-024026 | A | 1/1997 |
| JP | 2008-051663 | A | 3/2008 |
| JP | 2008-136673 | A | 6/2008 |
| JP | 2010-172739 | A | 8/2010 |
| JP | 2014-204779 | A | 10/2014 |
| JP | 2015-112223 | A | 6/2015 |
| JP | 2016-221028 | A | 12/2016 |
| JP | 2017-106812 | A | 6/2017 |
| JP | 2019-063439 | A | 4/2019 |
| WO | 2007/040223 | A1 | 4/2007 |
| WO | 2007/120812 | A2 | 10/2007 |
| WO | 2008/106191 | A2 | 9/2008 |
| WO | 2014/028103 | A1 | 2/2014 |
| WO | 2014/093846 | A1 | 6/2014 |
| WO | 2015/099932 | A1 | 7/2015 |
| WO | 2017/015322 | A1 | 1/2017 |
| WO | 2019221202 | A1 | 11/2019 |
| WO | 2019221203 | A1 | 11/2019 |
| WO | 2019221204 | A1 | 11/2019 |
| WO | 2019221205 | A1 | 11/2019 |

OTHER PUBLICATIONS

International Search Report dated Sep. 3, 2019 for Application No. PCT/JP2019/024656 published as WO2019/245018.
Potentially related U.S. Appl. No. 17/128,668, filed Dec. 21, 2020 entitled "Medical Device and Method of Manufacturing the Same".
European Search Report for Application No. 19802757.5, dated Apr. 19, 2021.
International Search Report dated Jun. 25, 2019 for Application No. PCT/JP2019/019396 published as WO2019221205.
Potentially related U.S. Appl. No. 15/823,794, filed Nov. 28, 2017 entitled "Medical Liquid-Pressure-Detecting Device", issued as U.S. Pat. No. 10,775,252 on Sep. 15, 2020.
Potentially related U.S. Appl. No. 17/093,817, filed Nov. 10, 2020 entitled "Pressure Detector," Published as WO2019221202.
Potentially related U.S. Appl. No. 17/093,821, filed Nov. 10, 2020 entitled "Pressure Detector," Published as WO2019221203.
Potentially related U.S. Appl. No. 17/093,823, filed Nov. 10, 2020 entitled "Pressure Detector," Published as WO2019221204.

[Fig. 1]
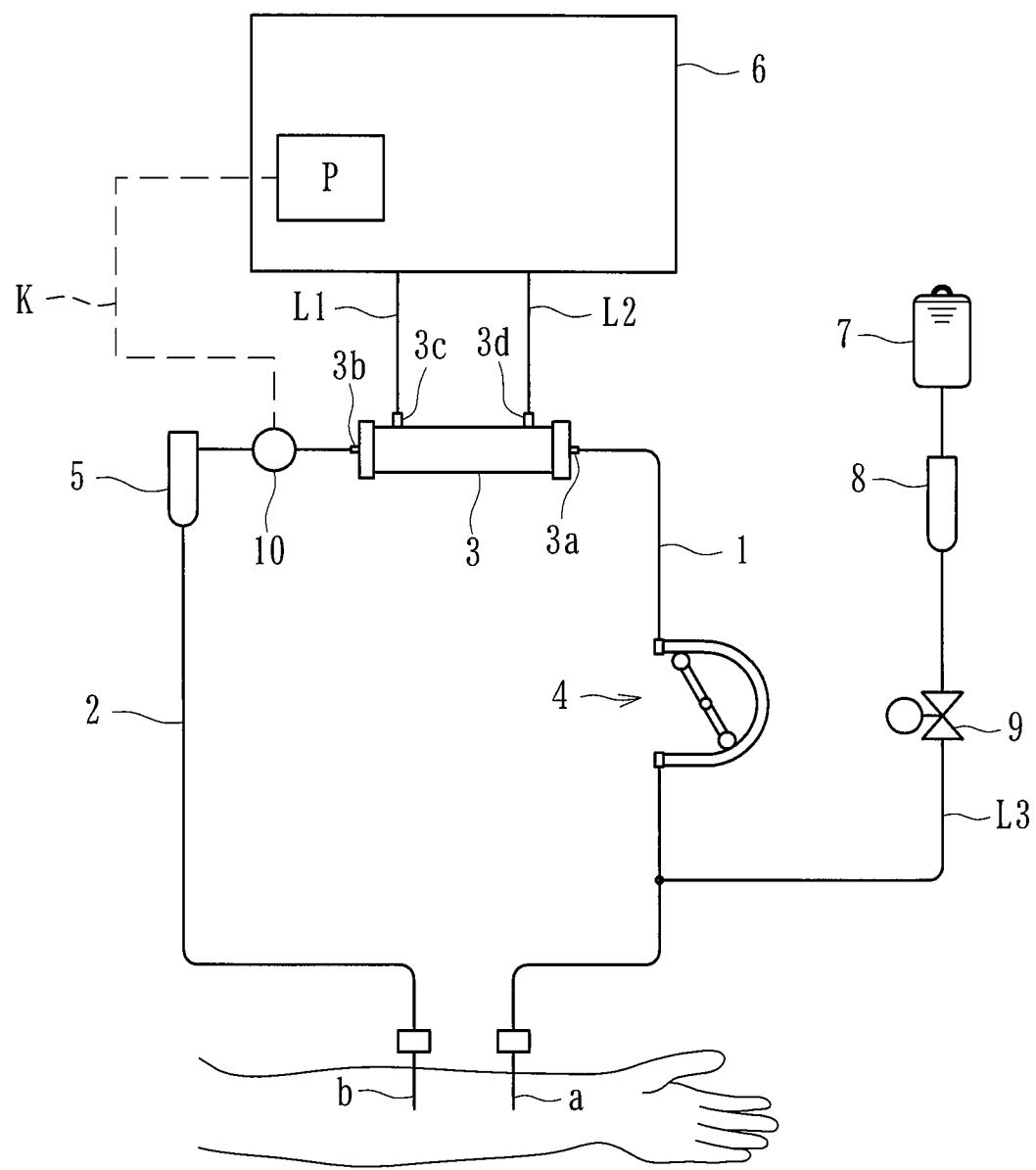

[Fig. 2]
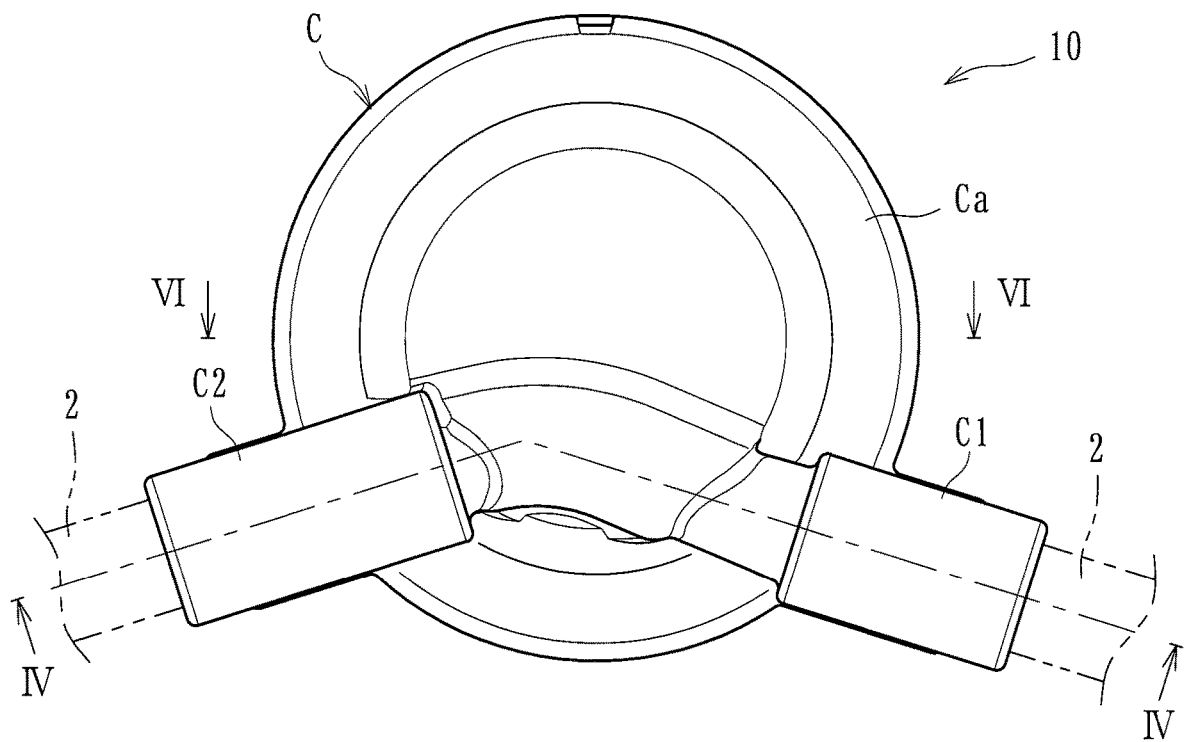
[Fig. 3]
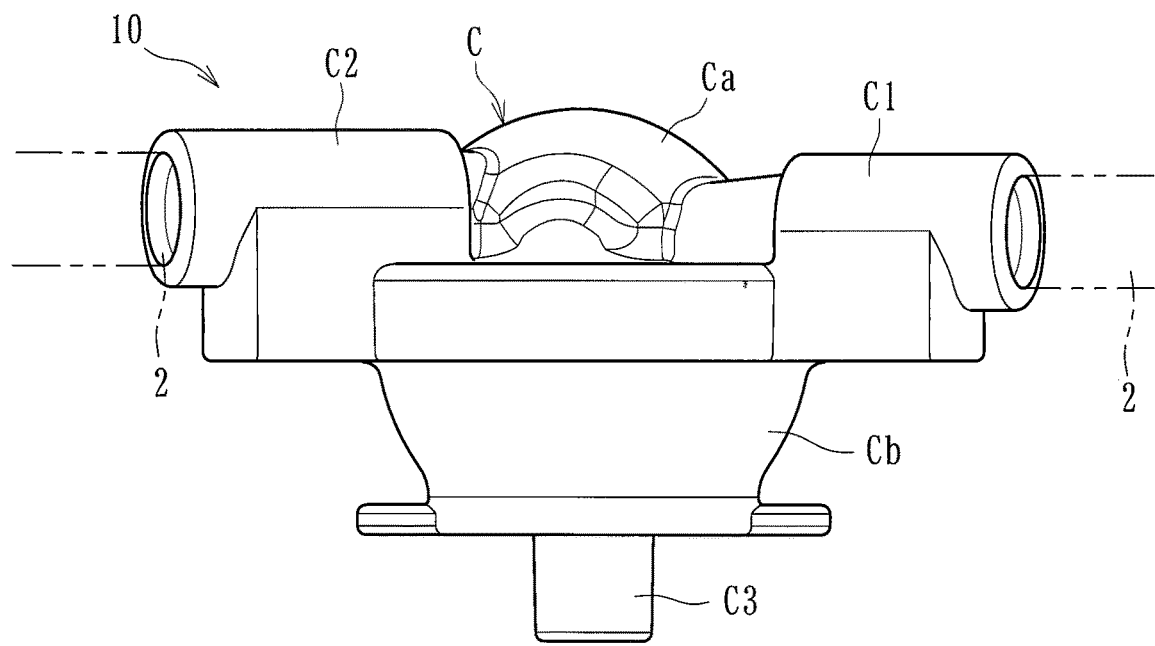

[Fig. 4]
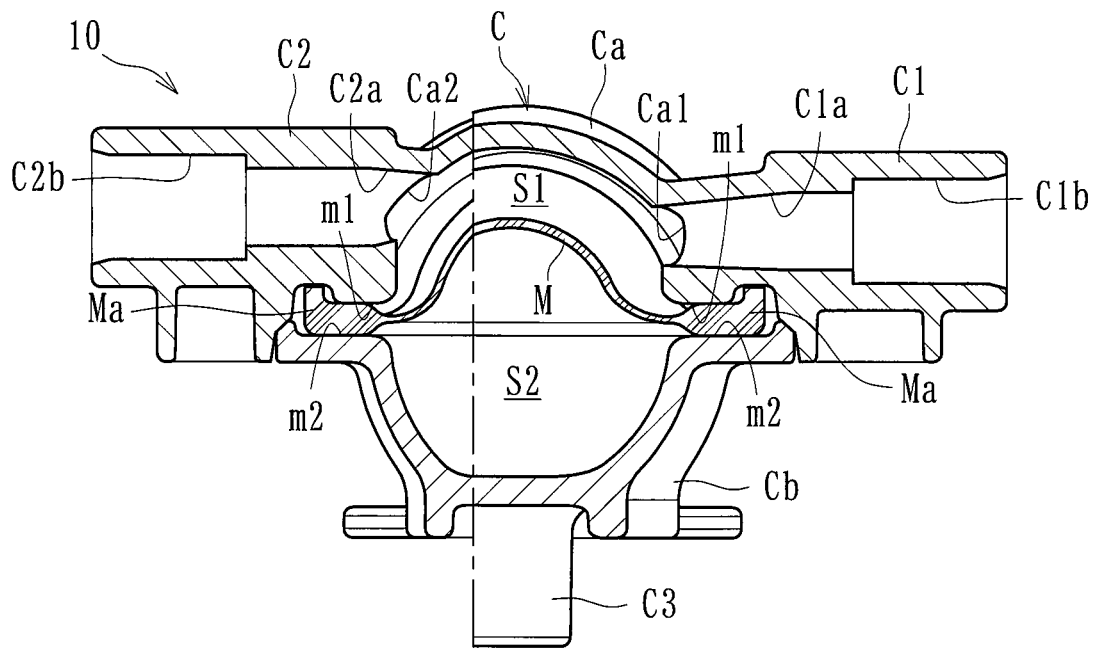
[Fig. 5]
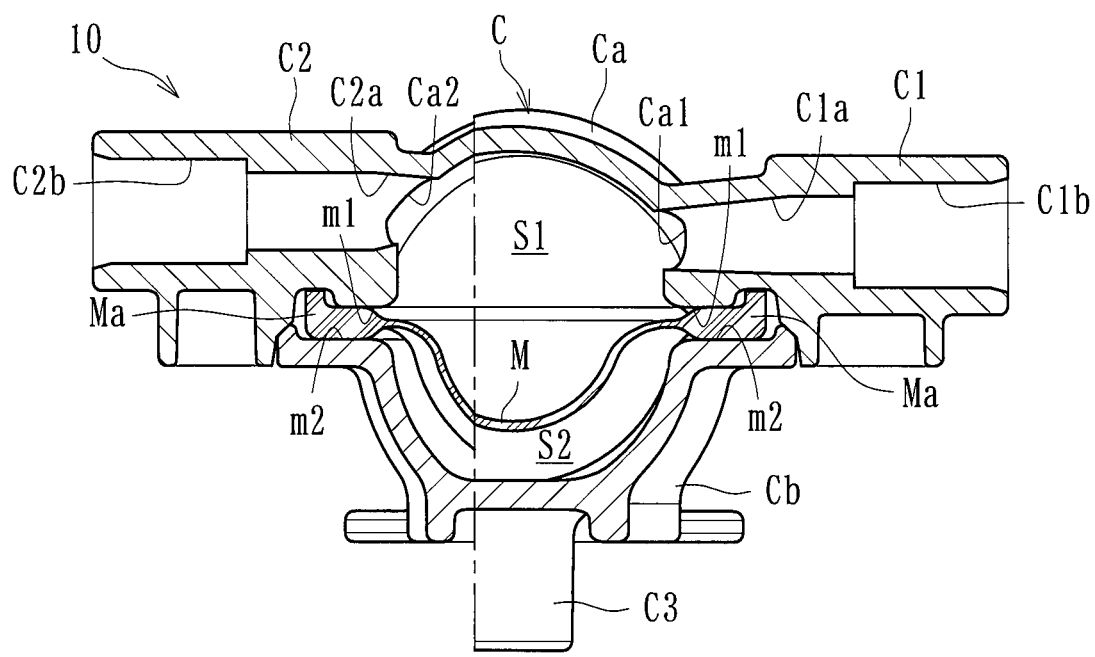

[Fig. 6]
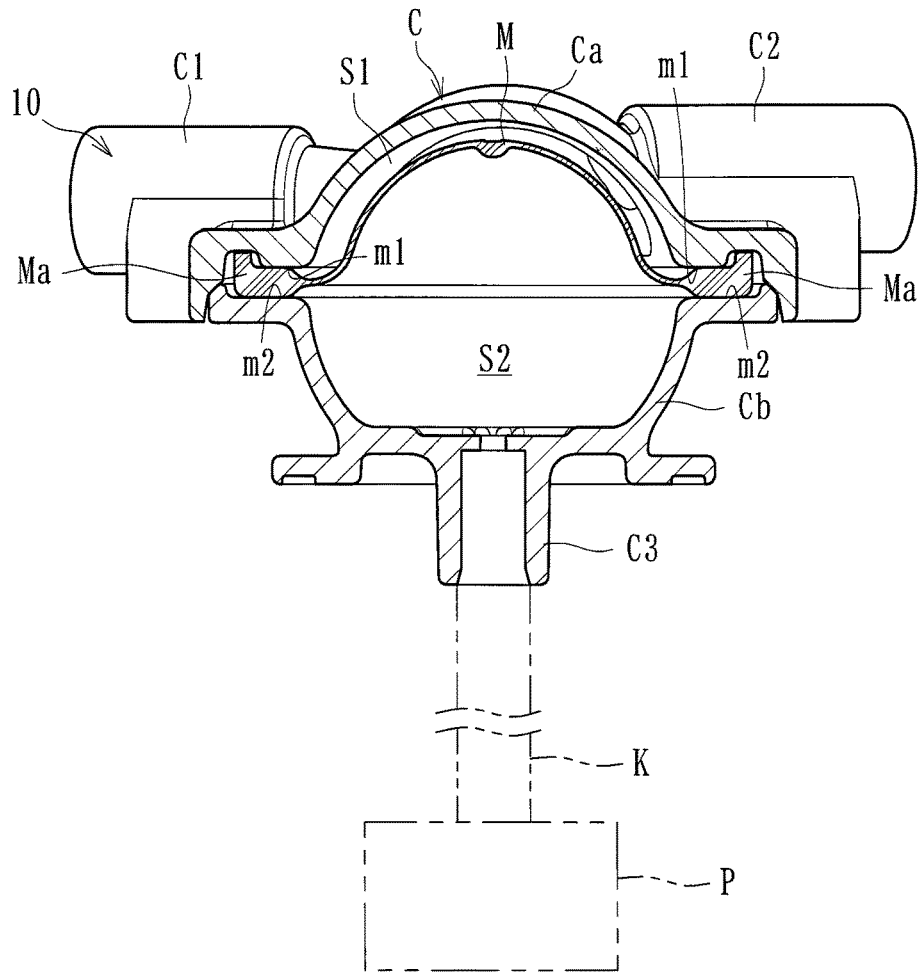
[Fig. 7]
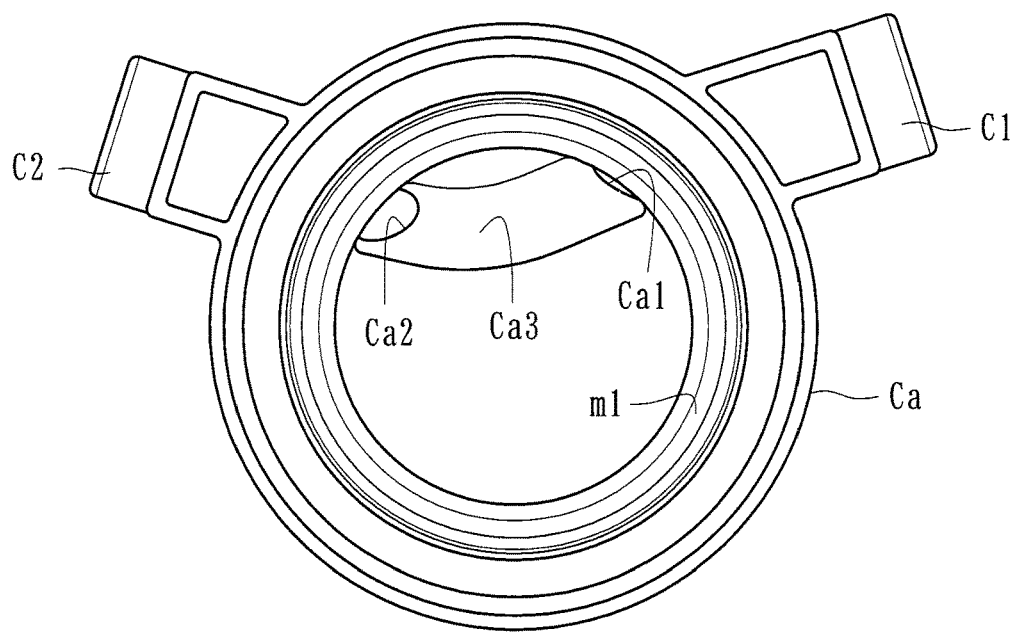

[ Fig. 8 ]
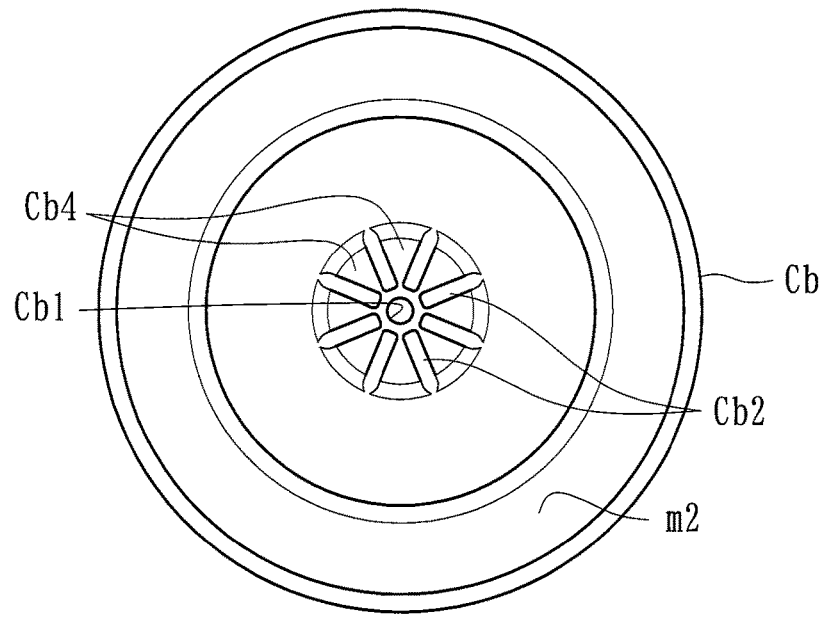
[ Fig. 9 ]
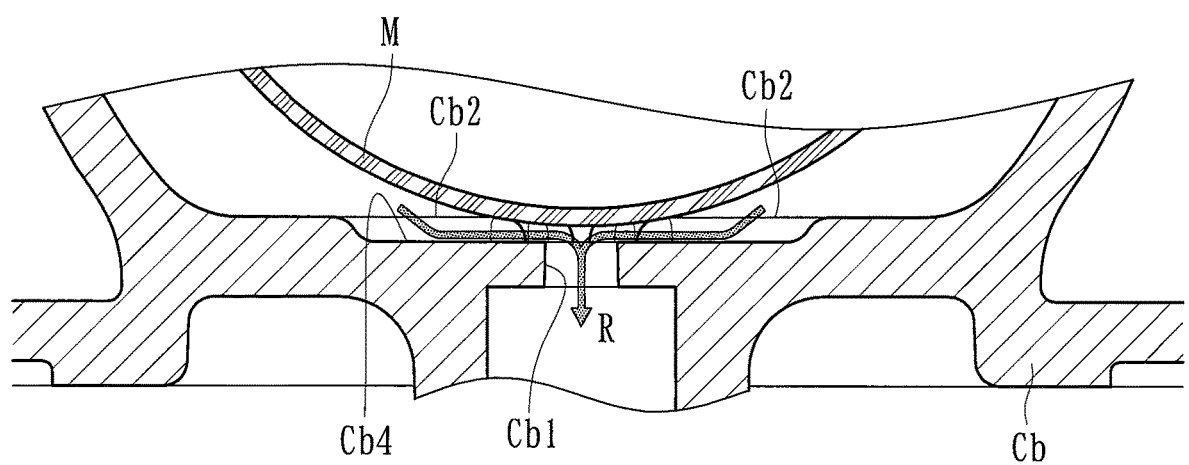

[Fig. 10]
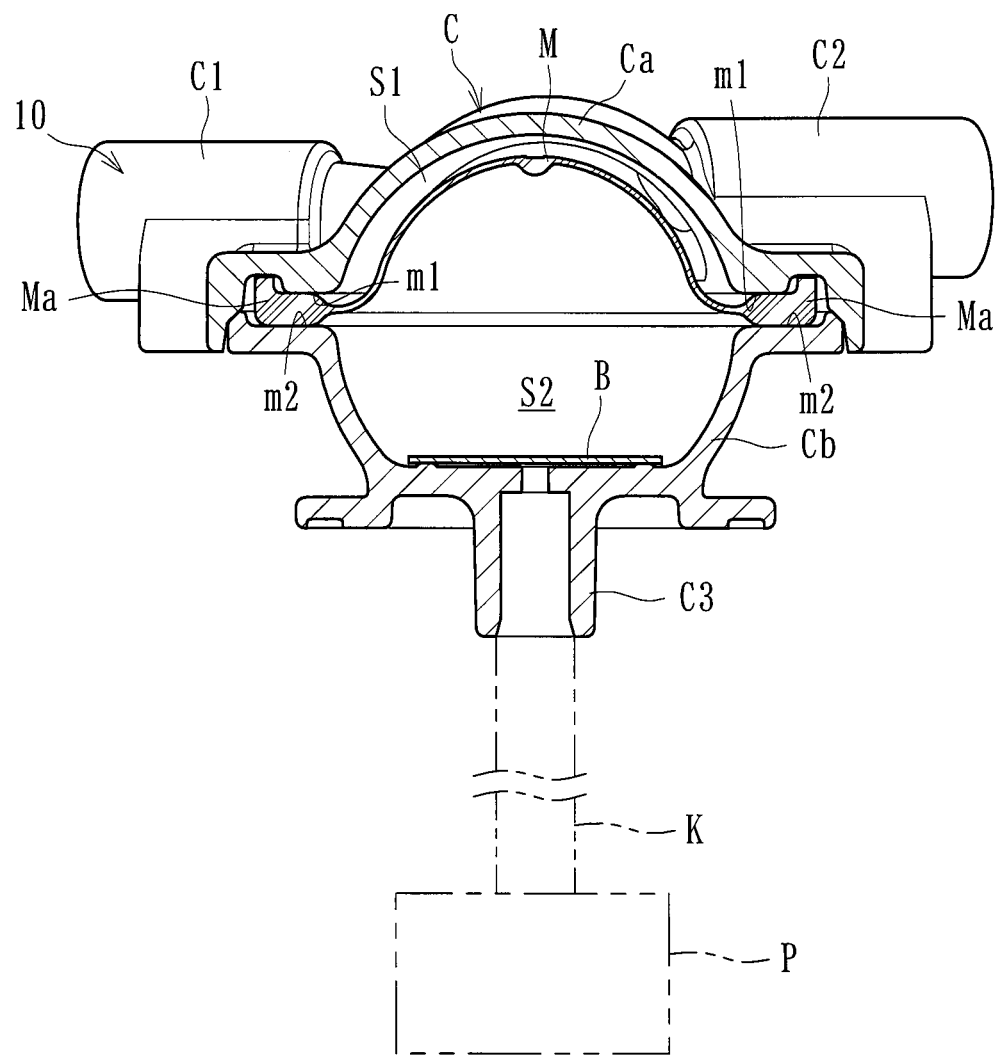

[ Fig. 11 ]
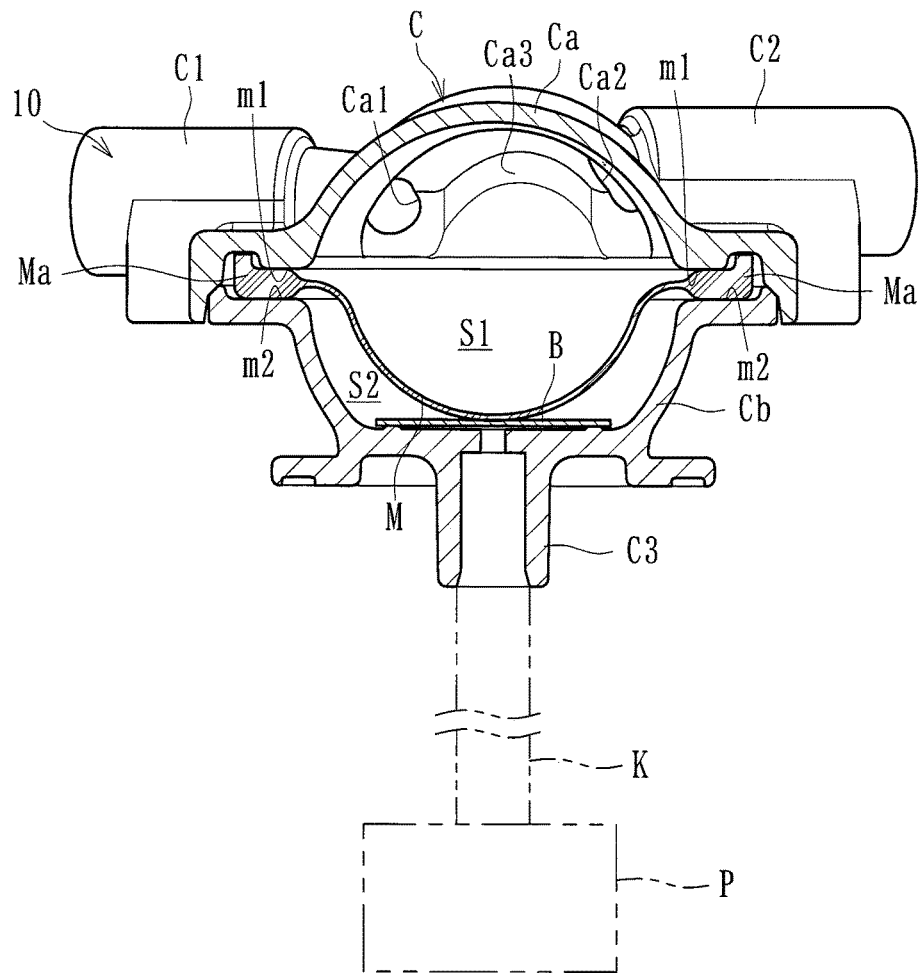
[ Fig. 12 ]
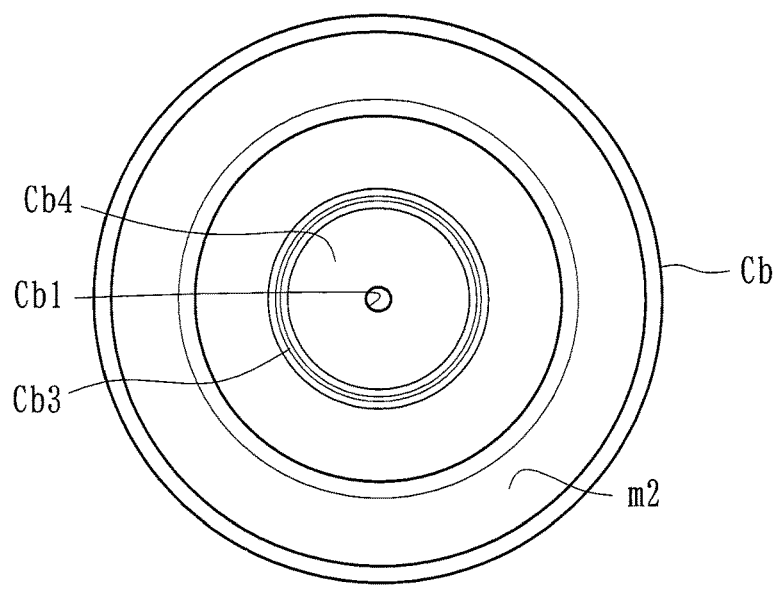

[Fig. 13]
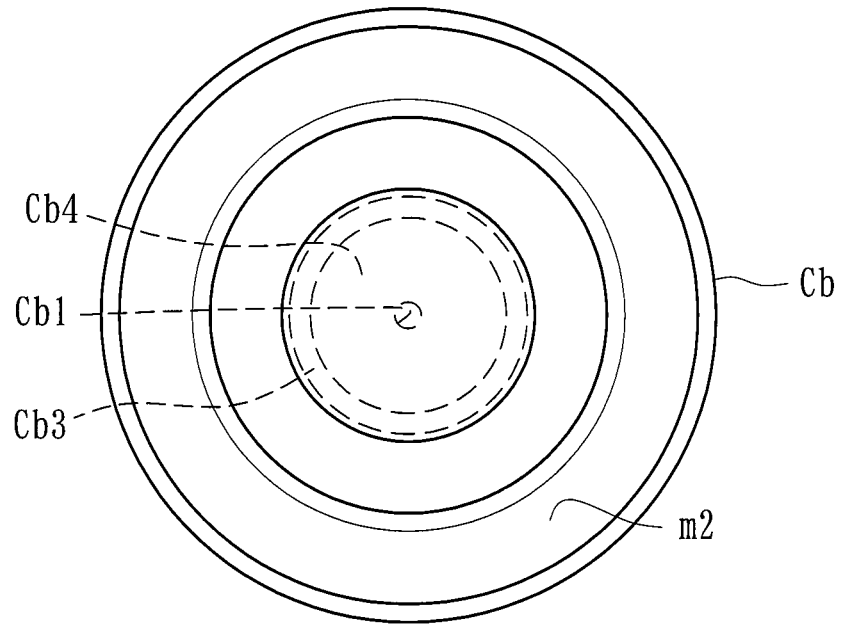
[Fig. 14]
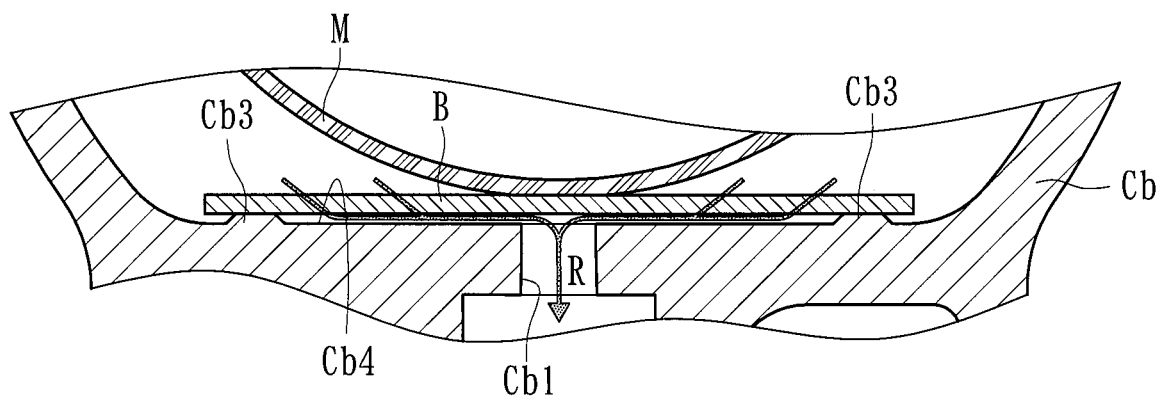
[Fig. 15]
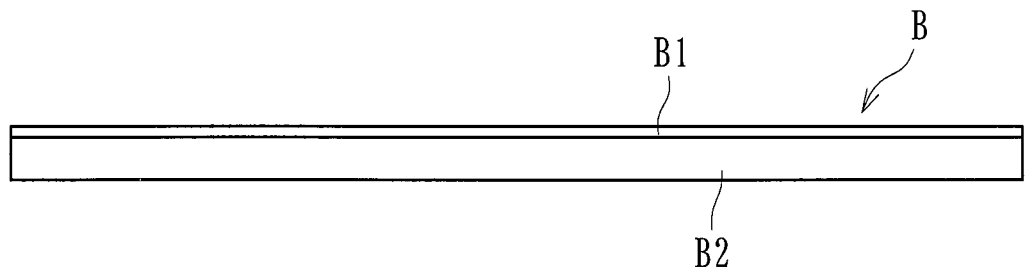

[Fig. 16]
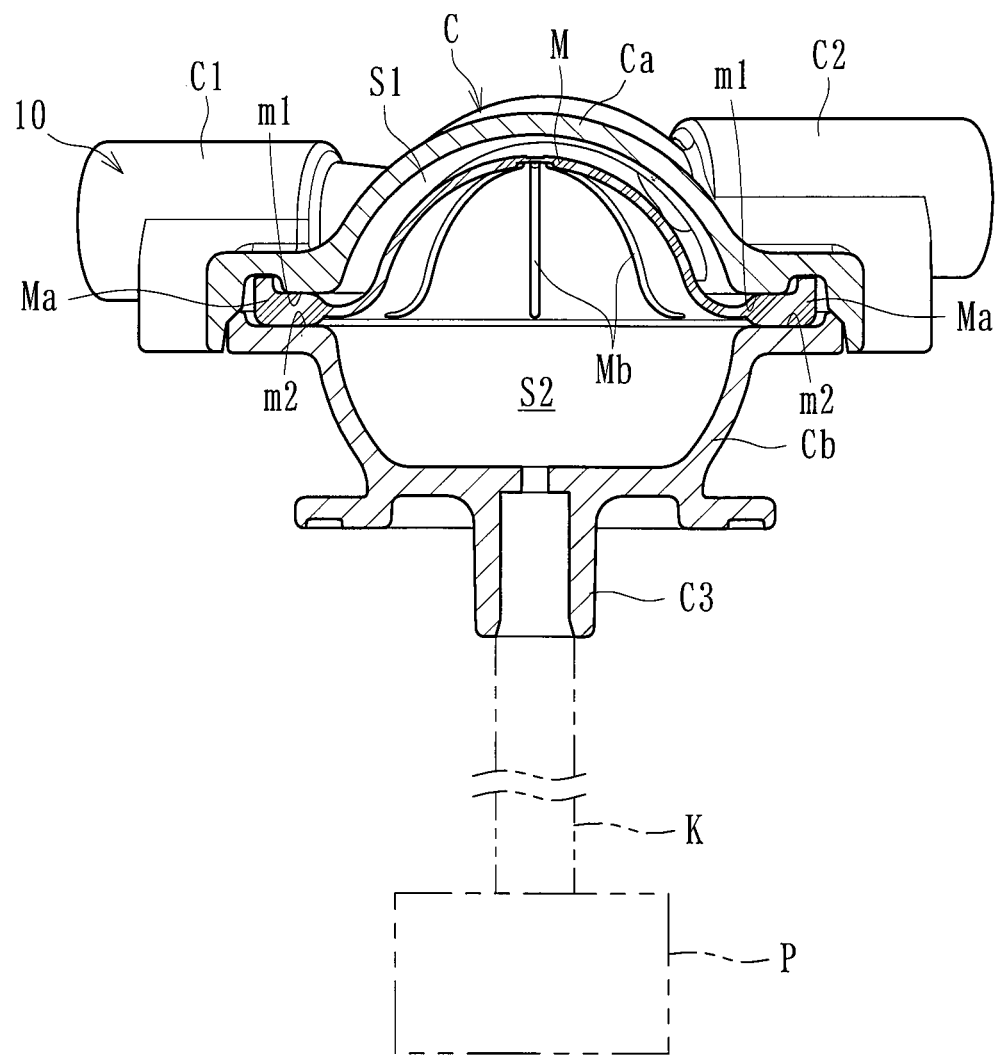

[ Fig. 17 ]
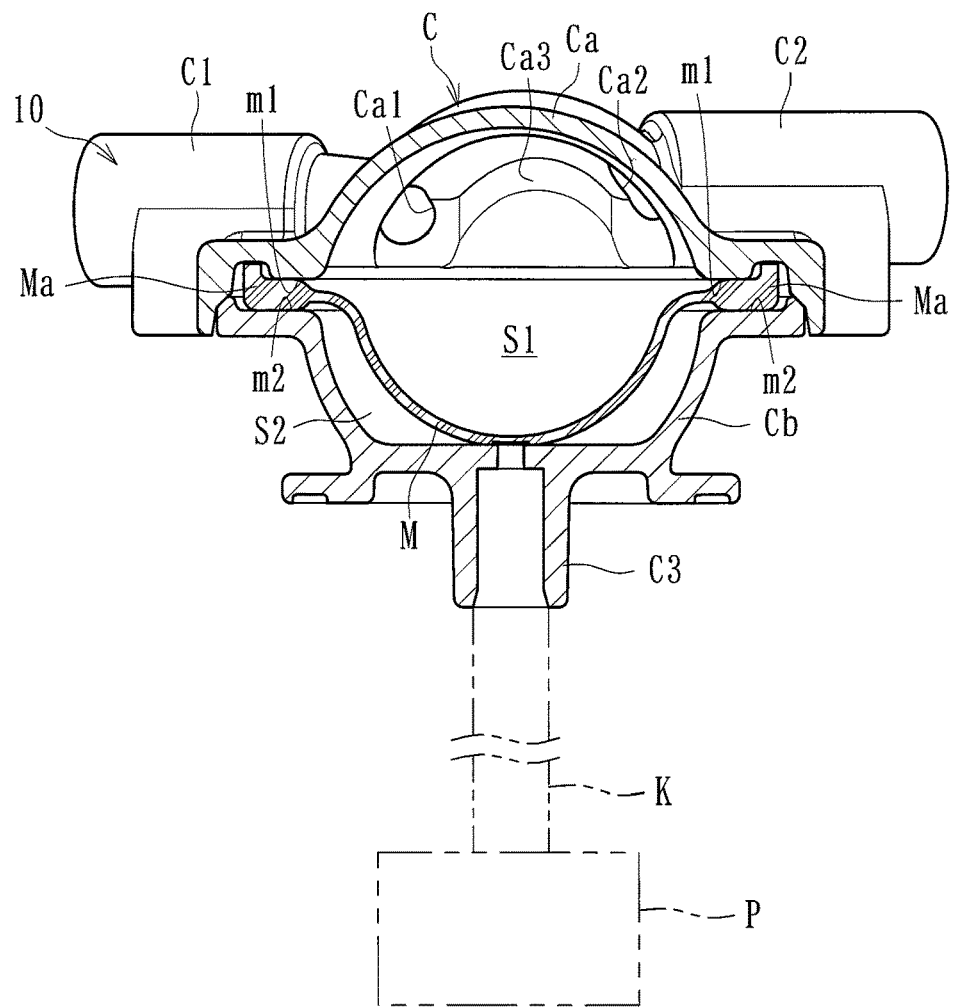
[ Fig. 18 ]
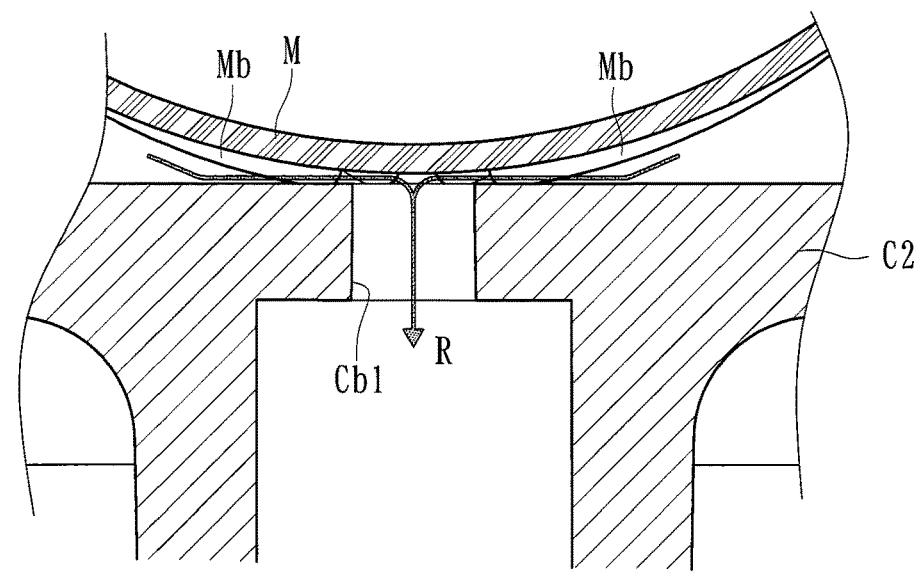

PRESSURE DETECTOR

CROSS-REFERENCE TO RELATED APPLICATION(S)

This application is a continuation of International Application No. PCT/JP2019/019396, filed on May 15, 2019, which claims priority to Japanese Application No. 2018-094465, filed on May 16, 2018, the entire disclosures of which are hereby incorporated by reference.

FIELD

The present invention relates to a pressure detector capable of detecting the pressure of liquid in a flow route by detecting the pressure in a gas-phase portion.

BACKGROUND

In general, dialysis treatment is performed by using a blood circuit for causing blood collected from a patient to extracorporeally circulate and return into the body. Such a blood circuit basically includes an arterial blood circuit and a venous blood circuit that are connectable to a dialyzer (a blood purifier) including, for example, hollow fiber membranes. The arterial blood circuit and the venous blood circuit are provided at distal ends thereof with an arterial puncture needle and a venous puncture needle, respectively. The patient is punctured with the puncture needles, and extracorporeal circulation of blood in the dialysis treatment is thus performed.

To detect the pressure of blood that extracorporeally circulates through a blood circuit, a pressure detector has been proposed as disclosed by PTL 1, for example. The pressure detector includes a case connectable to a blood circuit, and a diaphragm (a membrane member) provided in the case and with which a liquid-phase portion to be supplied with blood in the blood circuit and a gas-phase portion to be supplied with air are separated from each other, the diaphragm being displaceable in accordance with the pressure of the blood supplied to the liquid-phase portion, the pressure detector being capable of detecting the pressure of the blood by detecting the pressure in the gas-phase portion with a pressure detection sensor. With such a known pressure detector, since the liquid-phase portion and the gas-phase portion are separated from each other by the membrane member, the pressure of the blood in the blood circuit can be detected accurately while the blood is prevented from coming into contact with the air in the gas-phase portion.

PTL 1: Japanese Unexamined Patent Application Publication(Translation of PCT Application) No. 2017-504389 the teachings of which are expressly incorporated by reference herein for all purposes.

SUMMARY

In the above known pressure detector, however, when the membrane member is displaced toward the side of the gas-phase portion in accordance with the pressure in the liquid-phase portion, an opening provided in the gas-phase portion and communicating with the pressure detection sensor may be closed. Specifically, the opening may be closed before the limit of displacement of the membrane member is reached. In such an event, no further pressure change caused by the displacement of the membrane member cannot be detected, resulting in a narrow measurement range. If the capacity of the gas-phase portion is increased, a predetermined measurement range can be obtained even if the opening is closed during the displacement of the membrane member. In such a case, however, the capacity of the gas-phase portion becomes unnecessarily large, increasing the size of the case.

The present invention has been conceived in view of the above circumstances and provides a pressure detector in which a required measurement range can be obtained while the increase in the capacity of the gas-phase portion is suppressed.

Variation 1 may comprise a pressure detector that includes a case connectable to a flow route for liquid, and a membrane member provided in the case and with which a liquid-phase portion to be supplied with the liquid in the flow route and a gas-phase portion to be supplied with gas are separated from each other, the membrane member being displaceable in accordance with a pressure of the liquid supplied to the liquid-phase portion, the pressure detector detecting the pressure of the liquid in the flow route by detecting a pressure in the gas-phase portion. The gas-phase portion has an opening through which the gas is allowed to be introduced or discharged in accordance with the displacement of the membrane member, and a secured portion secured for the introduction or discharge of the gas through the opening during the displacement of the membrane member toward a side of the gas-phase portion.

Variation 2 may comprise the pressure detector according to variation 1 or any variation herein, the secured portion is a passage communicating with the opening and is secured for the introduction or discharge of the gas through the opening such that the gas is allowed to flow through the passage during the displacement of the membrane member toward the side of the gas-phase portion.

Variation 3 may comprise the pressure detector according to variation 2 or any variation herein, the passage is defined by a rib or a groove provided around the opening of the gas-phase portion.

Variation 4 may comprise the pressure detector according to variation 2 or any variation herein, the passage is defined by a combination of a recess provided around the opening of the gas-phase portion, and an allowing member that covers the recess inclusive of the opening and allows the gas to pass through.

Variation 5 may comprise the pressure detector according to variation 4 or any variation herein, the allowing member is a hydrophobic membrane that allows gas to pass through but blocks liquid from passing through.

Variation 6 may comprise the pressure detector according to variation 2 or any variation herein, the passage is defined by a rib or a groove provided on a surface of the membrane member, the surface facing the gas-phase portion.

Variation 7 may comprise a blood circuit to which the pressure detector according to any of variations 1 to 6 is connected.

Variation 8 may comprise the gas-phase portion has the opening through which gas is allowed to be introduced or discharged in accordance with the displacement of the membrane member, and the secured portion secured for the introduction or discharge of the gas through the opening during the displacement of the membrane member toward the side of the gas-phase portion. Therefore, a required measurement range can be obtained while the increase in the capacity of the gas-phase portion is suppressed.

Variation 9 may comprise any of the variations herein and the secured portion is a passage communicating with the opening and is secured for the introduction or discharge of the gas through the opening such that the gas is allowed to flow therethrough during the displacement of the membrane member toward the side of the gas-phase portion. Therefore, the opening can be assuredly prevented from being closed during the displacement of the membrane member toward the side of the gas-phase portion.

Variation 10 may comprise any of the variations herein and the passage is defined by the rib or the groove provided around the opening of the gas-phase portion. Therefore, the closing of the opening can be assuredly prevented by a simple configuration.

Variation 11 may comprise any of the variations herein and the passage is defined by the combination of the recess provided around the opening of the gas-phase portion, and the allowing member that covers the recess inclusive of the opening and allows gas to pass therethrough. Therefore, the area of the allowing member where gas is allowed to pass can be set large. Accordingly, the resistance at the passage of the gas is reduced. Thus, the deterioration in the accuracy of pressure detection can be suppressed.

Variation 12 may comprise any of the variations herein and the allowing member is the hydrophobic membrane that allows gas to pass therethrough but blocks liquid from passing therethrough. Therefore, even if there is any leakage of the liquid from the liquid-phase portion, the leaked liquid can be prevented from reaching the outside of the gas-phase portion.

Variation 13 may comprise any of the variations herein and the passage is defined by the rib or the groove provided on the surface of the membrane member that faces the gas-phase portion. Therefore, the closing of the opening can be assuredly prevented by a simple configuration.

Variation 14 may comprise any of the variations herein and a blood circuit producing the advantageous effects of the pressure detector according to any of variations 1 to 6 or 8 to 13 can be provided.

BRIEF DESCRIPTION OF THE DRAWINGS

FIG. 1 is a schematic diagram illustrating a dialysis apparatus (a blood purification apparatus) to which a pressure detector according to a first embodiment of the present invention is applied.

FIG. 2 is a plan view of the pressure detector.

FIG. 3 is a front view of the pressure detector.

FIG. 4 is a sectional view taken along line IV-IV illustrated in FIG. 2 (with a membrane member displaced toward the side of a liquid-phase portion).

FIG. 5 is a sectional view taken along line IV-IV illustrated in FIG. 2 (with the membrane member displaced toward the side of a gas-phase portion).

FIG. 6 is a sectional view taken along line VI-VI illustrated in FIG. 2.

FIG. 7 is a plan view of an inlet opening and an outlet opening provided in a liquid-phase-portion case included in the pressure detector.

FIG. 8 is a plan view of a gas-phase-portion case included in the pressure detector.

FIG. 9 is a sectional view of passages provided in the pressure detector.

FIG. 10 is a sectional view of a pressure detector according to a second embodiment of the present invention (with a membrane member displaced toward a liquid-phase portion).

FIG. 11 is a sectional view of the pressure detector (with the membrane member displaced toward a gas-phase portion).

FIG. 12 is a plan view of a gas-phase-portion case included in the pressure detector (with a hydrophobic membrane yet to be attached thereto).

FIG. 13 is a plan view of the gas-phase-portion case included in the pressure detector (with the hydrophobic membrane attached thereto).

FIG. 14 is a sectional view of passages provided in the pressure detector.

FIG. 15 is a schematic view illustrating a section of the hydrophobic membrane included in the pressure detector.

FIG. 16 is a sectional view of a pressure detector according to a third embodiment of the present invention (with a membrane member displaced toward a liquid-phase portion).

FIG. 17 is a sectional view of the pressure detector (with the membrane member displaced toward a gas-phase portion).

FIG. 18 is a sectional view of passages provided in the pressure detector.

DETAILED DESCRIPTION

Embodiments of the present invention will now be described specifically with reference to the drawings.

A blood purification apparatus applied to a first embodiment is a dialysis apparatus for giving dialysis treatment and basically includes, as illustrated in FIG. 1, a blood circuit including an arterial blood circuit 1 and a venous blood circuit 2, a dialyzer 3 (a blood purifier) provided between the arterial blood circuit 1 and the venous blood circuit 2 and that purifies blood flowing through the blood circuit, a blood pump 4, an air-trap chamber 5 provided to the venous blood circuit 2, a dialysis device 6 that supplies dialysate to the dialyzer 3 and drains waste liquid from the dialyzer 3, a physiological-saline supply line L3 (a substitution-fluid supply line) that allows physiological saline as a substitution fluid to be supplied to the blood circuit, and a storage unit 7 that stores the physiological saline as the substitution fluid.

The arterial blood circuit 1 is provided with an arterial puncture needle (a) connectable to a distal end thereof through a connector, and the blood pump 4, which is of a peristaltic type, at a halfway position thereof. The venous blood circuit 2 is provided with a venous puncture needle (b) connectable to a distal end thereof through a connector, and the air-trap chamber 5 at a halfway position thereof. The air-trap chamber 5 is capable of trapping bubbles in the liquid and is provided with a filtering net (not illustrated), thereby being capable of trapping, for example, thrombi and the like at the time of blood return. In this specification, a side on which the puncture needle for blood removal (blood collection) is provided is referred to as the "arterial" side, and a side on which the puncture needle for blood return is provided is referred to as the "venous" side. The "arterial" side and the "venous" side are not defined in accordance with which of the artery and the vein is to be the object of puncture.

The blood pump 4, which is a peristaltic pump provided to the arterial blood circuit 1, is capable of undergoing normal rotation and reverse rotation and causing the liquid in the blood circuit to flow in the direction of rotation thereof. Specifically, the arterial blood circuit 1 includes a squeezable tube that is softer and has a larger diameter than flexible tubes forming the other portions of the arterial blood circuit 1. The blood pump 4 includes rollers for squeezing the squeezable tube in the direction of liquid delivery. When the blood pump 4 is activated, the rollers rotate and thus squeeze the squeezable tube (a portion of the blood circuit), whereby the liquid in the tube can be made to flow in the direction of rotation (the direction in which the rollers rotate).

When the blood pump 4 is activated to undergo normal rotation (leftward rotation in the drawing) while a patient is punctured with the arterial puncture needle (a) and the venous puncture needle (b), the patient's blood flows through the arterial blood circuit 1 and reaches the dialyzer 3, where the blood is purified. Then, the blood flows through the venous blood circuit 2 while undergoing bubble removal in the air-trap chamber 5 and returns into the patient's body. That is, the patient's blood is purified with the dialyzer 3 while being caused to extracorporeally circulate through the blood circuit from the distal end of the arterial blood circuit 1 to the distal end of the venous blood circuit 2. When the blood pump 4 is activated to undergo reverse rotation (rightward rotation in the drawing), the blood in the blood circuit (a portion of the arterial blood circuit 1 that is between the distal end and a position where the blood pump 4 is provided) can be returned to the patient.

The dialyzer 3 has, in a housing thereof, a blood introduction port 3a, a blood delivery port 3b, a dialysate introduction port 3c, and a dialysate delivery port 3d. The blood introduction port 3a is connected to the arterial blood circuit 1. The blood delivery port 3b is connected to the venous blood circuit 2. The dialysate introduction port 3c and the dialysate delivery port 3d are connected to a dialysate introduction line L1 and a dialysate drain line L2, respectively, extending from the dialysis device 6.

The dialyzer 3 houses a plurality of hollow fibers. Spaces inside the respective hollow fibers form flow routes for blood, and spaces between the inner surface of the housing and the outer surfaces of the hollow fibers form flow routes for dialysate. The hollow fibers each have a number of microscopic holes (pores) extending therethrough from the outer surface to the inner surface, thereby forming a hollow fiber membrane. Impurities and the like contained in the blood are allowed to permeate through the hollow fiber membranes into the dialysate.

On the other hand, the dialysis device 6 includes a liquid delivery unit such as a duplex pump provided over the dialysate introduction line L1 and the dialysate drain line L2. A bypass line that bypasses the liquid delivery unit is provided with an ultrafiltration pump for removing water from the patient's blood flowing in the dialyzer 3. One end of the dialysate introduction line L1 is connected to the dialyzer 3 (the dialysate introduction port 3c), and the other end is connected to a dialysate supply device (not illustrated) that prepares a dialysate at a predetermined concentration. One end of the dialysate drain line L2 is connected to the dialyzer 3 (the dialysate delivery port 3d), and the other end is connected to a drainage unit, not illustrated. The dialysate supplied from the dialysate supply device flows through the dialysate introduction line L1 into the dialyzer 3, and further flows through the dialysate drain line L2 into the drainage unit.

The air-trap chamber 5 is provided with an overflow line extending from the top thereof. The overflow line is provided with a clamp unit, such as an electromagnetic valve, at a halfway position thereof. When the clamp unit such as an electromagnetic valve is opened, the liquid (a priming solution or the like) flowing in the blood circuit can be made to overflow through the overflow line.

The physiological-saline supply line L3 (the substitution-fluid supply line) is connected at one end thereof to the arterial blood circuit 1 between the position where the blood pump 4 is provided and the distal end of the arterial blood circuit 1 through a T-shaped pipe or the like. The physiological-saline supply line L3 forms a flow route (such as a flexible tube or the like) through which the physiological saline (the substitution fluid) to substitute for the blood in the blood circuit is allowed to be supplied to the arterial blood circuit 1. The physiological-saline supply line L3 is provided at the other end thereof with the storage unit 7 (a so-called "saline bag"), in which a predetermined amount of physiological saline is stored. The physiological-saline supply line L3 is further provided at a halfway position thereof with an air-trap chamber 8.

The physiological-saline supply line L3 according to the present embodiment is further provided with a clamp unit 9 (such as an electromagnetic valve or the like). The clamp unit 9 is capable of opening and closing the physiological-saline supply line L3, thereby closing and opening the flow route. The state of the physiological-saline supply line L3 is switchable as intended by opening or closing the clamp unit 9, between a closed state where the flow route is closed and an open state where the physiological saline (substitution fluid) is allowed to flow. The clamp unit 9 may be replaced with a general-purpose device such as a pair of forceps with which the flow route of the physiological-saline supply line L3 can be manually closed and opened.

The blood circuit applied to the present embodiment is provided with a pressure detector 10. The pressure detector 10 is connected to the venous blood circuit 2 at a position between the dialyzer 3 and the air-trap chamber 5 and is capable of detecting the pressure of the blood flowing in the venous blood circuit 2 (the blood circuit). Specifically, as illustrated in FIGS. 2 to 6, the pressure detector 10 includes a case C connectable to the flow route for liquid (in the present embodiment, the venous blood circuit 2 (the blood circuit)), and a membrane member M provided in the case C and with which a liquid-phase portion S1 to be supplied with the liquid in the flow route (in the present embodiment, the blood in the venous blood circuit 2 (the blood circuit)) and a gas-phase portion S2 to be supplied with air are separated from each other, the membrane member M being displaceable in accordance with the pressure of the liquid (blood) supplied to the liquid-phase portion S1. The pressure detector 10 is capable of detecting the pressure of the liquid in the flow route (the venous blood circuit 2) by detecting the pressure in the gas-phase portion S2 with a pressure detection sensor P.

The case C is a hollow molded component obtained by molding a specified resin material or the like. The case C is a combination of a liquid-phase-portion case Ca defining the liquid-phase portion S1 and a gas-phase-portion case Cb defining the gas-phase portion S2. The liquid-phase-portion case Ca has an inlet port C1 and an outlet port C2 integrally molded therewith. The inlet port C1 and the outlet port C2 are each connectable to the flow route for liquid and allow the flow route to communicate with the liquid-phase portion S1. The gas-phase-portion case Cb has a connection port C3 integrally molded therewith. The connection port C3 is connectable to one end of a pipe K, to be described below, and allows the one end to communicate with the gas-phase portion S2. The functions of the inlet port C1 and the outlet port C2 of introducing and discharging the liquid may be switched therebetween (that is, the liquid may be discharged from the inlet port C1 while being introduced into the outlet port C2).

The liquid-phase-portion case Ca has an annular holding surface m1 (see FIG. 7) at the periphery thereof. The gas-phase-portion case Cb has an annular holding surface m2 (see FIG. 8) at the periphery thereof. When the liquidphase-portion case Ca and the gas-phase-portion case Cb are mated to each other, a rim Ma of the membrane member M is placed between the holding surface m1 and the holding surface m2. Thus, the membrane member M can be attached in a sealing manner. A space thus provided in the case C is separated (sectioned) by the membrane member M into the liquid-phase portion S1 and the gas-phase portion S2.

The membrane member M serves as a diaphragm provided in the case C and is made of a flexible material that is displaceable or deformable in conformity with pressure change occurring in the liquid-phase portion S1 or the gas-phase portion S2. Specifically, if the pressure of the liquid (the hydraulic pressure) in the liquid-phase portion S1 is low, as illustrated in FIG. 4, the membrane member M is displaced toward the side of the liquid-phase portion S1, whereby the capacity of the gas-phase portion S2 is increased. If the pressure of the liquid (the hydraulic pressure) in the liquid-phase portion S1 is high, as illustrated in FIG. 5, the membrane member M is displaced toward the side of the gas-phase portion S2, whereby the capacity of the gas-phase portion S2 is reduced.

The gas-phase-portion case Cb has an opening Cb1 (see FIG. 8) substantially at the center of the bottom thereof. The opening Cb1 provided in the inner surface (the bottom) of the gas-phase-portion case Cb allows the flow route in the connection port C3 and the gas-phase portion S2 to communicate with each other. Accordingly, air (gas) is allowed to be introduced into or discharged from the gas-phase portion S2 in accordance with the displacement of the membrane member M. The pipe K is connected at one end thereof to the connection port C3 and at the other end thereof to the pressure detection sensor P. Therefore, as air (gas) is introduced or discharged through the opening Cb1 with the displacement of the membrane member M, the pressure detection sensor P can detect the pressure in the gas-phase portion S2. Note that the connection port C3 is not limited to the one to be connected to the pipe K and may be connected to another element capable of transmitting the pressure in the gas-phase portion S2 to the pressure detection sensor P.

The gas-phase-portion case Cb according to the present embodiment has recesses Cb4 surrounding the opening Cb1 provided at the bottom thereof, and an annular ridge Cb3 provided at the periphery thereof on the outer side with respect to the recesses Cb4. Furthermore, as illustrated in FIG. 8, the gas-phase portion S2 has a plurality of ribs Cb2 in the recesses Cb4 and around the opening Cb1. The ribs Cb2 project radially about the opening Cb1 and thus define passages R (secured portions).

The passages R (the secured portions) according to the present embodiment are secured for the introduction or discharge of the gas through the opening Cb1 during the displacement of the membrane member M toward the side of the gas-phase portion S2. As illustrated in FIG. 9, in a state where the membrane member M displaced toward the side of the gas-phase portion S2 is in contact with the ribs Cb2, the passages R are provided as spaces (spaces in the recesses Cb4) provided around the opening Cb1 and communicating with the opening Cb1. That is, during the displacement of the membrane member M toward the side of the gas-phase portion S2, gaps between the ribs Cb2 serve as the passages R, through which the gas (air in the gas-phase portion S2) is allowed to flow. Thus, the introduction or discharge of the gas through the opening Cb1 is ensured. Note that the ribs Cb2 for providing the passages R may be replaced with grooves provided around the opening Cb1 of the gas-phase portion S2.

The inlet port C1 according to the present embodiment is a portion (a projected portion) connectable to the flow route for liquid (the blood circuit) and includes, as illustrated in FIG. 6, a flow-route portion C1a through which the liquid (blood) flows into an inlet opening Ca1 (see FIG. 7) of the liquid-phase portion S1, and a connecting portion C1b connectable to the flow route (the blood circuit). Specifically, the flow-route portion C1a and the connecting portion C1b are continuous with each other in the axial direction thereof in the projected portion forming the inlet port C1. When a tube forming the flow route is connected to the connecting portion C1b, the liquid in the flow route can be made to flow into the flow-route portion C1a and then into the liquid-phase portion S1 through the inlet opening Ca1. Note that the inlet port C1 may be shaped as a recess to which the tube forming the flow route is to be connected.

The outlet port C2 according to the present embodiment is a portion (a projected portion) connectable to the flow route for liquid (the blood circuit) and includes, as illustrated in the drawing, a flow-route portion C2a through which the liquid (blood) having flowed into the liquid-phase portion S1 is discharged from an outlet opening Ca2 (see FIG. 7), and a connecting portion C2b connectable to the flow route (the blood circuit). Specifically, the flow-route portion C2a and the connecting portion C2b are continuous with each other in the axial direction thereof in the projected portion forming the outlet port C2. When a tube forming the flow route is connected to the connecting portion C2b, the liquid having flowed into the liquid-phase portion S1 can be made to flow into the flow-route portion C2a and then to be discharged to a flow route (the blood circuit) on the downstream side. Note that the outlet port C2 may be shaped as a recess to which the tube forming the flow route is to be connected.

According to the present embodiment, the gas-phase portion S2 has the opening Cb1 through which gas is allowed to be introduced or discharged in accordance with the displacement of the membrane member M, and the passages R (the secured portions) secured for the introduction or discharge of the gas through the opening Cb1 during the displacement of the membrane member M toward the side of the gas-phase portion S2. Therefore, a required measurement range can be obtained while the increase in the capacity of the gas-phase portion S2 is suppressed. The passages R (the secured portions) according to the present embodiment are spaces communicating with the opening Cb1 and are secured for the introduction or discharge of the gas through the opening Cb1 such that the gas is allowed to flow therethrough during the displacement of the membrane member M toward the side of the gas-phase portion S2. Therefore, the opening Cb1 can be assuredly prevented from being closed during the displacement of the membrane member M toward the side of the gas-phase portion S2.

In particular, the passages R according to the present embodiment are defined by the ribs Cb2 (or grooves) provided around the opening Cb1 of the gas-phase portion S2. Therefore, the closing of the opening Cb1 can be assuredly prevented by a simple configuration. Note that the ribs Cb2 for providing the passages R may be replaced with a ridge having another shape (such as a whirl shape). Furthermore, according to the present embodiment, a blood circuit producing the above advantageous effects of the pressure detector 10 can be provided.

Now, a pressure detector according to a second embodiment of the present invention will be described.

The pressure detector according to the present embodiment is applied to the same blood purification apparatus as that of the first embodiment. As illustrated in FIG. 1, the pressure detector is connected to the arterial blood circuit 1 between the distal end (the connector to which the arterial puncture needle (a) is connected) and the position where the blood pump 4 is provided, and is capable of detecting the pressure of the blood flowing in the arterial blood circuit 1.

As illustrated in FIGS. 10 to 15, a pressure detector 10 according to the present embodiment includes a case C connectable to the flow route for liquid (corresponding to the arterial blood circuit 1 in the present embodiment), and a membrane member M provided in the case C and with which a liquid-phase portion S1 to be supplied with the liquid in the flow route (in the present embodiment, the blood in the arterial blood circuit 1) and a gas-phase portion S2 to be supplied with air are separated from each other, the membrane member M being displaceable in accordance with the pressure of the liquid (blood) supplied to the liquid-phase portion S1. The pressure detector 10 is capable of detecting the pressure of the liquid in the flow route (the arterial blood circuit 1) by detecting the pressure in the gas-phase portion S2 with a pressure detection sensor P. Elements that are the same as those described in the first embodiment are denoted by corresponding ones of the reference numerals, and detailed description of those elements is omitted.

The passages R according to the present embodiment are secured for the introduction or discharge of the gas through the opening Cb1 during the displacement of the membrane member M toward the side of the gas-phase portion S2. The passages R are defined by a combination of the recesses Cb4 provided around the opening Cb1 of the gas-phase portion S2, and the hydrophobic membrane B (an allowing member) that covers the recesses Cb4 inclusive of the opening Cb1 and allows gas to pass therethrough. The hydrophobic membrane B is a member formed as a membrane that allows gas to pass therethrough but blocks liquid from passing therethrough. The periphery of the hydrophobic membrane B is welded (for example, by ultrasonic welding or the like) to the ridge Cb3 provided around the opening Cb1.

More specifically, as illustrated in FIG. 15, the hydrophobic membrane B according to the present embodiment includes a first layer B1 formed as a sheet (film) of a resin material of PTFE (polytetrafluoroethylene), and a second layer B2 formed as a nonwoven fabric of PEs (polyester) or the like. The first layer B1 and the second layer B2 are stacked in the thicknesswise direction thereof. In the present embodiment, the total thickness of the first layer B1 and the second layer B2 is about 0.1 to 0.5 mm, with the thickness of the first layer B1 (PTFE) being about one tenth of the total thickness.

The hydrophobic membrane B according to the present embodiment is obtained by pasting a sheet of PTFE, which serves as the first layer B1, on the surface of the second layer B2, which serves as a base. Alternatively, another type of hydrophobic membrane B (such as the one including a base made of a different material, or the one including no base) may be employed. The first layer B1 only needs to have a characteristic of allowing gas to pass therethrough but blocking liquid from passing therethrough and may be made of, for example, an acrylic copolymer, polyethersulfone, or the like.

During the displacement of the membrane member M toward the side of the gas-phase portion S2, as illustrated in FIG. 14, the hydrophobic membrane B secures the passages R, which allow the gas (air in the gas-phase portion S2) to flow therethrough (see the arrow illustrated in the drawing). Thus, the introduction or discharge of the gas through the opening Cb1 is ensured. The hydrophobic membrane B according to the present embodiment allows gas to pass therethrough but blocks liquid from passing therethrough. However, the hydrophobic membrane B only needs to cover the recesses Cb4 inclusive of the opening Cb1 and allow gas to pass therethrough.

According to the present embodiment, the gas-phase portion S2 has the opening Cb1 through which gas is allowed to be introduced or discharged in accordance with the displacement of the membrane member M, and the passages R (the secured portions) secured for the introduction or discharge of the gas through the opening Cb1 during the displacement of the membrane member M toward the side of the gas-phase portion S2. Therefore, a required measurement range can be obtained while the increase in the capacity of the gas-phase portion S2 is suppressed. The passages R (the secured portions) according to the present embodiment are spaces communicating with the opening Cb1 and are secured for the introduction or discharge of the gas through the opening Cb1 such that the gas is allowed to flow therethrough during the displacement of the membrane member M toward the side of the gas-phase portion S2. Therefore, the opening Cb1 can be assuredly prevented from being closed during the displacement of the membrane member M toward the side of the gas-phase portion S2.

In particular, the passages R according to the present embodiment are defined by the combination of the recesses Cb4 provided around the opening Cb1 of the gas-phase portion S2, and the hydrophobic membrane B (the allowing member) that covers the recesses Cb4 inclusive of the opening Cb1 and allows gas to pass therethrough. Therefore, the area of the hydrophobic membrane B (the allowing member) where gas is allowed to pass can be set large. Accordingly, the resistance at the passage of the gas is reduced. Thus, the deterioration in the accuracy of pressure detection can be suppressed.

Furthermore, the allowing member according to the present embodiment is the hydrophobic membrane B that allows gas to pass therethrough but blocks liquid from passing therethrough. Therefore, even if there is any leakage of the liquid (blood) from the liquid-phase portion S1, the leaked liquid can be prevented from reaching the outside of the gas-phase portion S2. Furthermore, according to the present embodiment, a blood circuit producing the above advantageous effects of the pressure detector 10 can be provided.

Now, a pressure detector according to a third embodiment of the present invention will be described.

The pressure detector according to the present embodiment is applied to the same blood purification apparatus as that of the first embodiment. As illustrated in FIG. 1, the pressure detector is connected to the venous blood circuit 2 at a position between the dialyzer 3 and the air-trap chamber 5 and is capable of detecting the pressure of the blood flowing in the venous blood circuit 2 (the blood circuit).

As illustrated in FIGS. 16 to 18, a pressure detector 10 according to the present embodiment includes a case C connectable to the flow route for liquid (in the present embodiment, the venous blood circuit 2 (the blood circuit)), and a membrane member M provided in the case C and with which a liquid-phase portion S1 to be supplied with the liquid in the flow route (in the present embodiment, the blood in the venous blood circuit 2 (the blood circuit)) and a gas-phase portion S2 to be supplied with air are separated from each other, the membrane member M being displaceable in accordance with the pressure of the liquid (blood) supplied to the liquid-phase portion S1. The pressure detector 10 is capable of detecting the pressure of the liquid in the flow route (the venous blood circuit 2) by detecting the pressure in the gas-phase portion S2 with a pressure detection sensor P. Elements that are the same as those described in the first embodiment are denoted by corresponding ones of the reference numerals, and detailed description of those elements is omitted.

The passages R according to the present embodiment are secured for the introduction or discharge of the gas through the opening Cb1 during the displacement of the membrane member M toward the side of the gas-phase portion S2. The passages R are defined by ribs Mb (or grooves) provided on a surface of the membrane member M that faces the gas-phase portion S2. Specifically, the ribs Mb (grooves), which are integrally formed on the surface of the membrane member M that faces the gas-phase portion S2, are arranged radially from the center toward the periphery of the membrane member M. During the displacement of the membrane member M toward the side of the gas-phase portion S2, as illustrated in FIG. 18, gaps between the ribs Mb serve as the passages R, which allow the gas (air in the gas-phase portion S2) to flow therethrough (see the arrow illustrated in the drawing). Thus, the introduction or discharge of the gas through the opening Cb1 is ensured.

According to the present embodiment, the gas-phase portion S2 has the opening Cb1 through which gas is allowed to be introduced or discharged in accordance with the displacement of the membrane member M, and the passages R (the secured portions) secured for the introduction or discharge of the gas through the opening Cb1 during the displacement of the membrane member M toward the side of the gas-phase portion S2. Therefore, a required measurement range can be obtained while the increase in the capacity of the gas-phase portion S2 is suppressed. The passages R (the secured portions) according to the present embodiment are spaces communicating with the opening Cb1 and are secured for the introduction or discharge of the gas through the opening Cb1 such that the gas is allowed to flow therethrough during the displacement of the membrane member M toward the side of the gas-phase portion S2. Therefore, the opening Cb1 can be assuredly prevented from being closed during the displacement of the membrane member M toward the side of the gas-phase portion S2.

In particular, the passages R according to the present embodiment are defined by the ribs Mb (or grooves) provided on the surface of the membrane member M that faces the gas-phase portion S2. Therefore, the closing of the opening Cb1 can be assuredly prevented by a simple configuration. Note that the ribs Mb for providing the passages R may be replaced with a ridge having another shape (such as a whirl shape). Furthermore, according to the present embodiment, a blood circuit producing the above advantageous effects of the pressure detector 10 can be provided.

While the embodiments have been described above, the present invention is not limited thereto. The ribs Cb2 according to the first embodiment may be provided over the entirety of the inner surface of the gas-phase-portion case Cb. Furthermore, the ribs Mb according to the third embodiment may be provided only in a portion facing the opening Cb1. Furthermore, in the first embodiment, the recesses Cb4 provided with the ribs Cb2 may be covered by the hydrophobic membrane B according to the second embodiment.

Furthermore, while the pressure detector 10 according to the first and third embodiments is connected to the venous blood circuit 2, the pressure detector 10 may be connected to another position of the blood circuit (for example, as the second embodiment, a position of the arterial blood circuit 1 between the distal end and the blood pump 4, or a position of the arterial blood circuit 1 between the blood pump 4 and the dialyzer 3). The blood circuit to which the present pressure detector 10 is to be connected may be of another type. For example, the blood circuit may be provided with not the air-trap chamber 5 but the present pressure detector 10 instead.

While the above embodiments each concern the pressure detector 10 provided to the blood circuit intended for dialysis treatment, the present invention may be applied to a pressure detector provided to another blood circuit to be used in a treatment of purifying blood of a patient. For example, the present invention may be applied to a pressure detector provided to a blood circuit to be used in acetate-free biofiltration (AFBF), continuous slow hemofiltration, hemoadsorption, selective cytapheresis, plasma exchange, double filtration plasmapheresis, plasma adsorption, or the like.

The present invention is applicable to any pressure detector of any other type or for any other use, as long as a gas-phase portion has an opening through which gas is allowed to be introduced or discharged in accordance with the displacement of a membrane member, and a secured portion secured for the introduction or discharge of the gas through the opening during the displacement of the membrane member toward the side of the gas-phase portion.

REFERENCE SIGN LIST 1 arterial blood circuit
2 venous blood circuit
3 dialyzer (blood purifier)
4 blood pump
5 air-trap chamber
6 dialysis device
7 storage unit
8 air-trap chamber
9 clamp unit
10 pressure detector
L1 dialysate introduction line
L2 dialysate drain line
L3 physiological-saline supply line
C case
Ca liquid-phase-portion case
Ca1 inlet opening
Ca2 outlet opening
Cb gas-phase-portion case
Cb1 opening
Cb2 rib
Cb3 ridge
Cb4 recess
C1 inlet port
C1a flow-route portion
C1b connecting portion
C2 outlet port
C2a flow-route portion
C2b connecting portion
C3 connection port
M membrane member
P pressure detection sensor
S1 liquid-phase portion
S2 gas-phase portion
K pipe
B hydrophobic membrane
R passage (secured portion)

The invention claimed is:
1. A pressure detector comprising:
a case comprising:
a liquid-phase-portion-case and a gas-phase-portion-case, wherein the case is connectable to a flow route for liquid, and a membrane member provided in the case between the liquid-phase-portion-case and the gas-phase-portion-case so that the membrane member separates a liquid-phase portion to be supplied with the liquid in the flow route and a gas-phase portion to be supplied with gas, the membrane member being displaceable in accordance with a pressure of the liquid supplied to the liquid-phase portion, the pressure detector detecting the pressure of the liquid in the flow route by detecting a pressure in the gas-phase portion, wherein the gas-phase-portion-case has an opening through which the gas is allowed to be introduced or discharged in accordance with displacement of the membrane member, and a secured portion secured for introduction or discharge of the gas through the opening during the displacement of the membrane member towards the gas-phase-portion-case; and wherein the secured portion consist of recesses surrounding the opening and ribs formed in the recesses around the opening;

wherein the gas-phase-portion-case has a bottom wall and the secured portion is formed in the bottom wall and a top of the bottom wall and a top of the ribs are coplanar and the ribs extend into the secured portion so that the recesses are formed along the ribs; and wherein the membrane member, when moved into a state where the membrane member is displaced towards the gas-phase portion, contacts the ribs so that the recesses provide spaces that allow the gas to flow through the opening.

2. The pressure detector according to claim 1, wherein the ribs extend radially about the opening.

3. The pressure detector according to claim 1, wherein the ribs and recesses alternate around the opening.

4. The pressure detector according to claim 1, wherein during the introduction or the discharge of the gas relative to the opening, the gas travels parallel to the ribs.

5. The pressure detector according to claim 1, further comprising a hydrophobic membrane located between the bottom wall and the membrane member.

6. The pressure detector according to claim 1, further comprising:

a ridge in the bottom wall extending around the opening.

7. The pressure detector according to claim 6, wherein the ridge has a whirl shape.

8. The pressure detector according to claim 6, wherein the ridge is an annular ridge.

9. The pressure detector according to claim 8, wherein the annular ridge extends around the ribs.

10. The pressure detector according to claim 6, wherein the ridge extends around the recesses.

* * * * *